(12) United States Patent
Thomas

(10) Patent No.: US 10,335,973 B2
(45) Date of Patent: Jul. 2, 2019

(54) HYDRO-FORMED FILM WITH THREE-DIMENSIONAL MICRO-APERTURES

(71) Applicant: Tredegar Film Products Corporation, Richmond, VA (US)

(72) Inventor: Paul Eugene Thomas, Terre Haute, IN (US)

(73) Assignee: TREDEGAR FILM PRODUCTS CORPORATION, Richmond, VA (US)

( * ) Notice: Subject to any disclaimer, the term of this patent is extended or adjusted under 35 U.S.C. 154(b) by 27 days.

(21) Appl. No.: 15/374,567

(22) Filed: Dec. 9, 2016

(65) Prior Publication Data

US 2017/0165880 A1    Jun. 15, 2017

Related U.S. Application Data

(60) Provisional application No. 62/266,256, filed on Dec. 11, 2015.

(51) Int. Cl.
*B26F 1/26* (2006.01)
*A61F 13/511* (2006.01)
(Continued)

(52) U.S. Cl.
CPC .......... *B26F 1/26* (2013.01); *A61F 13/15731* (2013.01); *A61F 13/512* (2013.01);
(Continued)

(58) Field of Classification Search
None
See application file for complete search history.

(56) References Cited

U.S. PATENT DOCUMENTS 4,252,516 A * 2/1981 Raley .................... B29C 51/225
                                                    425/290
4,463,045 A    7/1984 Ahr et al.
(Continued)

FOREIGN PATENT DOCUMENTS

| EP | 0745367 A2 * | 12/1996 | ......... A61F 13/4942 |
| FR | 2763273 A1 * | 11/1998 | ....... A61F 13/15731 |
| WO | 9315701 | 8/1993 | |

OTHER PUBLICATIONS

Machine Translation of FR-2763273-A1, Nov. 1998 (Year: 1998).*

(Continued)

*Primary Examiner* — Jeffrey A Vonch
(74) *Attorney, Agent, or Firm* — Karceski IP Law, PLLC

(57) ABSTRACT

A method of processing a polymeric web includes providing a forming screen configured for supporting and moving with the web in a machine direction. The forming screen has a plurality of elliptical screen openings, each having a major axis perpendicular to the machine direction and a minor axis parallel to the machine direction. The method includes continuously depositing the web onto the forming screen and passing the web and forming screen through a water stream having a pressure level sufficient to cause the web to be forced into the screen openings, thereby forming protrusions extending from the planar surface of the web. Each protrusion has an apex, an opening at the apex, and an elliptical cross-section parallel to the planar surface of the web. The elliptical cross-section has a protrusion axis ratio that may be selected so as to produce a desired protrusion axis ratio.

12 Claims, 14 Drawing Sheets

(51) Int. Cl.

| | | |
|---|---|---|
| *A61F 13/512* | (2006.01) | |
| *A61F 13/513* | (2006.01) | |
| *B29C 41/26* | (2006.01) | |
| *B29C 41/28* | (2006.01) | |
| *B29C 41/38* | (2006.01) | |
| *B29C 41/50* | (2006.01) | |
| *A61F 13/15* | (2006.01) | |
| B29L 31/48 | (2006.01) | |
| B29K 101/12 | (2006.01) | |
| B29L 7/00 | (2006.01) | |
| B29C 51/10 | (2006.01) | |
| B29D 28/00 | (2006.01) | |

(52) U.S. Cl.
CPC ...... *A61F 13/5121* (2013.01); *A61F 13/5126* (2013.01); *A61F 13/51104* (2013.01); *B29C 41/26* (2013.01); *B29C 41/28* (2013.01); *B29C 41/38* (2013.01); *B29C 41/50* (2013.01); *A61F 13/5122* (2013.01); *A61F 2013/15284* (2013.01); *A61F 2013/15829* (2013.01); *A61F 2013/5127* (2013.01); *A61F 2013/51147* (2013.01); *A61F 2013/51338* (2013.01); *B29C 51/10* (2013.01); *B29C 2791/006* (2013.01); *B29C 2791/007* (2013.01); *B29C 2793/0045* (2013.01); *B29D 28/00* (2013.01); *B29K 2101/12* (2013.01); *B29L 2007/00* (2013.01); *B29L 2031/4878* (2013.01); *Y10T 428/24182* (2015.01); *Y10T 428/24281* (2015.01)

(56) References Cited

U.S. PATENT DOCUMENTS

| | | | | |
|---|---|---|---|---|
| 4,609,518 | A * | 9/1986 | Curro | A61F 13/15731 |
| | | | | 264/504 |
| 4,629,643 | A * | 12/1986 | Curro | A61F 13/5146 |
| | | | | 428/131 |
| 4,637,819 | A * | 1/1987 | Ouellette | A61F 13/5123 |
| | | | | 428/131 |
| 4,681,793 | A * | 7/1987 | Linman | A61F 13/51405 |
| | | | | 428/138 |
| 4,695,422 | A * | 9/1987 | Curro | A61F 13/15731 |
| | | | | 264/154 |
| 4,772,444 | A * | 9/1988 | Curro | A61F 13/5146 |
| | | | | 264/154 |
| 4,778,644 | A * | 10/1988 | Curro | A61F 13/5146 |
| | | | | 264/280 |
| 4,839,216 | A * | 6/1989 | Curro | A61F 13/15731 |
| | | | | 428/116 |
| 4,846,821 | A * | 7/1989 | Lyons | A61F 13/51476 |
| | | | | 604/369 |
| 5,158,819 | A * | 10/1992 | Goodman, Jr. | A61F 13/15731 |
| | | | | 264/154 |
| 5,562,932 | A | 10/1996 | Rieker | |
| 5,567,376 | A * | 10/1996 | Turi | A61F 13/15731 |
| | | | | 264/455 |
| 5,681,301 | A * | 10/1997 | Yang | A61F 13/15731 |
| | | | | 428/132 |
| 5,824,352 | A * | 10/1998 | Yang | A61F 13/15707 |
| | | | | 425/290 |
| 5,945,196 | A * | 8/1999 | Rieker | B26F 1/26 |
| | | | | 264/154 |
| 5,980,814 | A * | 11/1999 | Roller | A61F 13/00991 |
| | | | | 264/455 |
| 6,228,462 | B1 * | 5/2001 | Lee | A61F 13/512 |
| | | | | 428/131 |
| 6,534,141 | B1 * | 3/2003 | Hull, Jr. | B26F 1/26 |
| | | | | 428/131 |
| 6,570,059 | B1 * | 5/2003 | Carlucci | A61F 13/5146 |
| | | | | 604/367 |
| 6,599,612 | B1 * | 7/2003 | Gray | A61F 13/512 |
| | | | | 428/131 |
| 8,168,102 | B2 | 5/2012 | DiBerardino | |
| 8,460,778 | B2 | 6/2013 | Thomas et al. | |
| 2001/0044008 | A1 * | 11/2001 | O'Donnell | A61F 13/15731 |
| | | | | 428/131 |
| 2002/0133132 | A1 | 9/2002 | Copat et al. | |
| 2003/0003269 | A1 * | 1/2003 | Lee | A61F 13/15203 |
| | | | | 428/131 |
| 2004/0119207 | A1 * | 6/2004 | Stone | B26F 1/26 |
| | | | | 264/442 |
| 2004/0121120 | A1 * | 6/2004 | Gray | A61F 13/15731 |
| | | | | 428/131 |
| 2004/0161586 | A1 * | 8/2004 | Cree | A61F 13/537 |
| | | | | 428/131 |
| 2004/0195730 | A1 * | 10/2004 | van Weperen | B26F 1/26 |
| | | | | 264/400 |
| 2004/0227275 | A1 * | 11/2004 | Maschino | B26F 1/26 |
| | | | | 264/500 |
| 2004/0247833 | A1 * | 12/2004 | Copat et al. | A61F 13/15731 |
| | | | | 428/156 |
| 2006/0087053 | A1 * | 4/2006 | O'Donnell | B26F 1/18 |
| | | | | 264/156 |
| 2006/0141279 | A1 * | 6/2006 | Thuis | B26F 1/26 |
| | | | | 428/596 |
| 2008/0138574 | A1 * | 6/2008 | Maschino | A61F 13/512 |
| | | | | 428/137 |
| 2009/0299316 | A1 * | 12/2009 | Seyler | A61F 13/53713 |
| | | | | 604/378 |
| 2009/0302504 | A1 * | 12/2009 | Di Berardino | B26D 7/1863 |
| | | | | 264/413 |
| 2010/0121298 | A1 * | 5/2010 | Seyler | A61F 13/53713 |
| | | | | 604/378 |
| 2010/0151191 | A1 * | 6/2010 | Thomas | A61F 13/15707 |
| | | | | 428/137 |
| 2010/0230857 | A1 * | 9/2010 | Muhs | B29C 66/934 |
| | | | | 264/284 |
| 2010/0230858 | A1 * | 9/2010 | Stone | A61F 13/15731 |
| | | | | 264/293 |
| 2010/0230866 | A1 * | 9/2010 | Gray | B26F 1/26 |
| | | | | 264/504 |
| 2010/0230867 | A1 * | 9/2010 | Gray | B26F 1/26 |
| | | | | 264/504 |
| 2010/0233428 | A1 * | 9/2010 | Stone | A61F 13/15739 |
| | | | | 428/133 |
| 2010/0233438 | A1 * | 9/2010 | Stone | B26F 1/26 |
| | | | | 428/172 |
| 2011/0190686 | A1 * | 8/2011 | Hasse | A61F 13/26 |
| | | | | 604/15 |
| 2011/0221094 | A1 * | 9/2011 | Gross | A61F 13/15707 |
| | | | | 264/284 |
| 2012/0003423 | A1 * | 1/2012 | Cree | A61F 13/512 |
| | | | | 428/137 |
| 2012/0276331 | A1 * | 11/2012 | Orr | B29C 53/24 |
| | | | | 428/137 |
| 2012/0277701 | A1 | 11/2012 | Stone et al. | |
| 2015/0273793 | A1 | 10/2015 | Thomas | |
| 2016/0038351 | A1 * | 2/2016 | Cecchetto | B26F 1/20 |
| | | | | 428/134 |
| 2016/0039109 | A1 * | 2/2016 | Cecchetto | B26F 1/20 |
| | | | | 264/553 |
| 2016/0158074 | A1 * | 6/2016 | Norimoto | A61F 13/51104 |
| | | | | 604/378 |

OTHER PUBLICATIONS

International Search Report and Written Opinion dated Apr. 4, 2017, for International Patent Application No. PCT/US2016/065933.
International Preliminary Report on Patentability dated Jun. 21, 2018, for International Patent Application No. PCT/US2016/065933.

* cited by examiner

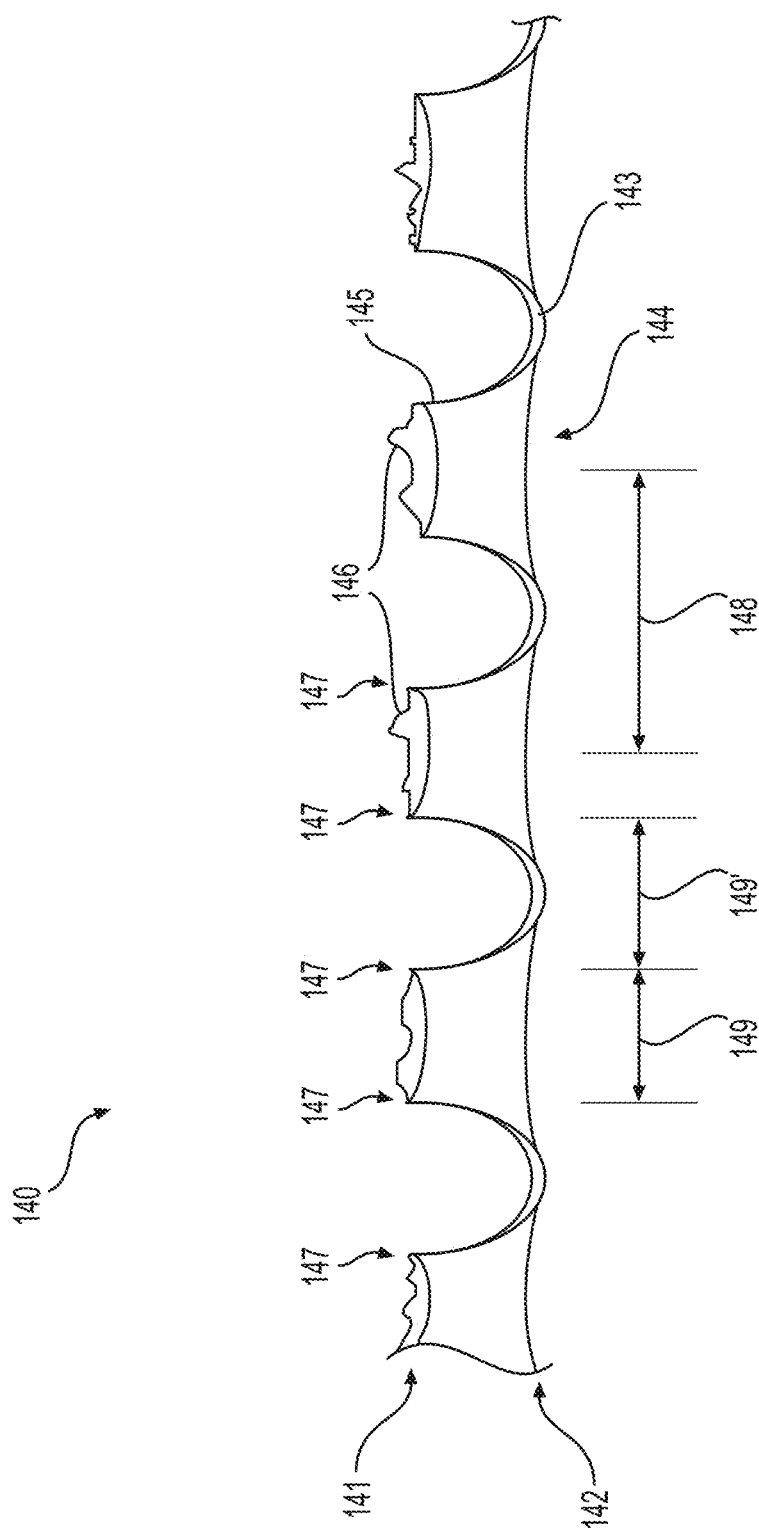

HYDRO-FORMED FILM WITH THREE-DIMENSIONAL MICRO-APERTURES

CROSS-REFERENCE TO RELATED APPLICATIONS

This application claims the benefit of priority from U.S. Provisional Patent Application No. 62/266,256, filed Dec. 11, 2015, the content of which is incorporated herein by reference in its entirety.

FIELD

The present invention relates generally to porous polymeric films useful in absorptive devices for the transmission of fluids. In particular, the present invention relates to films with three-dimensional micro-apertures in patterns of high mesh count of greater than 30 mesh which provide softness while also helping to reduce surface wetness after use.

BACKGROUND

Three-dimensional apertured formed film topsheets, or the acquisition distribution layer interposed between the topsheet and the core of absorptive devices, having both three-dimensional micro-apertures facing upward toward the skin side of users of absorptive devices and three-dimensional macro-apertures interspersed in a pattern within the field of three-dimensional micro-apertures, the macro-apertures facing downward toward the absorbent core, are well known in the art. The three-dimensional micro-apertures are known to provide a tactile impression of cottony soft, cloth-like or silky textures while also enhancing the reduction of the amount of surface wetness after use.

Such films may be produced using one of several methods, including vacuum-forming process and hydro-forming process. In both these methods, the film is deposited on a rotating screen having openings corresponding to a desired micro-aperture pattern. In vacuum-forming, a relative vacuum is established across the screen so that the film is drawn into the openings, thereby forming a series of protrusions on the film surface. If the vacuum differential is sufficient, an opening is formed in the film at the apex of each protrusion. In hydro-forming, similar protrusions are formed by directing a high pressure water stream at the side of the film opposite of the screen. The pressure of the water stream forces the film into the holes of the screen. If sufficient pressure is applied, an opening is formed in the film at the apex of each protrusion.

Micro-apertures can also be formed using mechanical methods such as needle punching, but such methods tend to require additional steps to provide the three dimensionality that tends to enhance the perceived softness of the final material.

In U.S. Pat. No. 4,609,518 to Curro et al. ("Curro '518"), a polymeric web can be produced using one or more three-dimensional forming structures, essentially a parent patent to the "hydro-forming process", it is taught that three-dimensional micro-aperture patterns of high mesh count are formed by a high pressure water stream ". . . having filaments [or lands]. . . ranging in diameter [or land width] from about 3 mils to about 7 mils and mesh counts ranging from about 140 by 140 per square inch to about 80 by 80 per square inch, respectively, will typically produce very soft feeling three-dimensional apertured webs when subjected to the high pressure liquid jet[s]. . . issuing from nozzle[s]. . . . The relatively small three-dimensional apertures created in such webs substantially correspond to the void spaces [or openings] created in the interstices . . . between the intersecting filaments [or lands]." The three-dimensional macro-apertures are then formed in a second stage process where that forming screen has large openings of a lower mesh count as designed to be suitable for adequate fluid acquisition through the topsheet into the absorbent core of absorptive device.

Premium ALWAYS° brand feminine hygiene pads, sold by Procter & Gamble Co., Ohio, utilize a topsheet substantially produced by the hydroforming process of Curro '518. The three-dimensional micro-aperture pattern, when counted from a purchased pad from any of a variety of Retail Stores, is generally around 100 mesh. It is known for its cottony soft tactile impression which renders both comfort and cleanliness to the user. When viewing the three-dimensional micro-apertures under magnification, they have an elongation, or major axis, in the machine direction (MD). The MD corresponds to the length or front-to-back direction of the feminine pad. Many are somewhat pointed at the extreme ends of their major axes. They appear in shape to be very similar to the iris of a 'cat-eye', thus here-in-after their shape will be known as a 'cat-eye' shape. This cat-eye shape is common for three-dimensional apertures formed in the hydroforming process of the prior art.

Three-dimensional macro-apertures can be formed into a 'precursor' web already comprising a pattern of softening three-dimensional micro-apertures. A second stage of hydroforming is used in Curro '518. Other methods use a roller with a pattern of needles, pins or similar protrusions with the protrusions being pushed through the precursor web into a malleable, easily penetrated material, or, ideally, into a corresponding pattern of depression such as grooves, slots or cavities. Typically the protruding direction of the micro-apertures is up and the protruding direction of the macro-apertures is down.

U.S. Pat. No. 8,168,102 to Di Berardino ("Di Berardino '102") discloses one mechanical punching method. In its abstract, it describes: "A machine utilized for producing and manufacturing a film, soft at touch, resilient and suitable at draining use. A film produced by such a machine, presents, at least, on one surface an essentially continuous pattern of micro-funnels three-dimensional (3D) directed in an essentially perpendicular way to the surface from which the micro-openings have origin. It presents also on the opposite surface a continuous pattern, composed by 3D macro-funnels directed in an essentially perpendicular way to the surface from which the macro-funnels have origin. The "micro-funnels" term, intend to describe a multitude of funnels non-distinguishable by the human eye at a distance equal or higher than 450 mm, while the "macro-funnels" term, intend to describe funnels clearly visible by the human eye at a distance higher than 450 mm."

Claim 9 of Di Berardino '102 further describes the method: "A device for forming a thermoplastic film with macro holes from a film already having micro holes, comprising: a first reel with multiple needles on its surface; a second reel with multiple grooves, the grooves coupled to the needles during the rotation of the first and second reels to obtain the macro holes; and a third reel with perforations, the perforations being coupled with the needles of the first reel during rotation of the first reel to remove the thermoplastic film from the first reel without substantially damaging the micro holes, wherein the third reel uses electrostatic electricity to remove the thermoplastic film from the first reel by exerting a force via the electrostatic electricity on the macro holes of the thermoplastic film."

U BY KOTEX® brand feminine napkins, sold by Kimberly-Clark Corporation, utilize this type of topsheet material and call it an Xpress DRI® cover. The three-dimensional micro-aperture pattern, when counted from a purchased pad from any of a variety of Retail Stores, is generally around 60 mesh. It is also known for its cottony soft tactile impression which renders both comfort and cleanliness to the user. When viewing the three-dimensional micro-apertures under magnification they are essentially round, as is common for three-dimensional apertures formed in a vacuum forming process.

Additionally, it is known that sufficient open area of the three-dimensional micro-apertured web, as with any three-dimensional apertured web, is required not only for adequate softness, but also to assist with fluid acquisition related to surface cleanliness after use. While the 100 mesh hydroformed pattern is proven to be sufficiently soft and clean, 100 mesh to about 75 mesh patterns will not form good three-dimensional aperture openings by the vacuum forming method due to its limited maximum pressure differential of slightly less than one negative atmosphere—about 14.0 PSI. Smaller openings require higher force to create an opening like the multiple hundreds PSI of hydro-forming. Therefore, the film's open area achievable by vacuum forming, virtually approaching zero percent as mesh counts increase beyond 75 mesh, is insufficient for good performance in reducing residual surface wetness after use. The smaller opening sizes and lack of thinning at the apex can also negatively affect the perception of softness.

Conversely, the lower mesh count versions in the range of micro-apertures from about 40 to about 75 mesh, that form good round openings with sufficient open area in the vacuum forming process, will not form openings with sufficient open area for fluid acquisition dynamics or sufficient softness properties when produced by the hydroforming process. Logically, the cat-eye shape of hydroforming, increasingly more dramatic within these micro-aperture mesh counts, where the forming screens have progressively larger openings, reduces the resulting film's open area. While a circle's major axis (i.e., its diameter) exists in all directions, the cat-eye shape (which may be an ellipse or other ovate figure) has a major axis value in one direction and a minor axis value in the other direction. Thus, the cat-eye shape has a lower opening area than a circle having the same major axis value. Hydro-forming also creates a smaller aperture in general, so its major axis will be less than the value of the circle's axis, which compounds the loss of open area.

This difference occurs primarily because, in vacuum forming methods, the polymer web is provided in molten form, and is therefore completely pliable and formable. As a result, the pressure differential due to the vacuum causes the molten material to mold itself against the walls of the aperture. In that last moment of being molten, it essentially forms an exact replicate of the screen aperture. As it cools to a solid state, however, it shrinks. This shrinkage reduces the film aperture dimensions to only a percentage of the screen aperture dimensions.

Conversely, hydro-forming processes involve placing a solid (i.e., non-molten) film web over the forming screen. Such a web requires a higher pressure differential to distort and re-shape the solid film into its new three dimensional aperture form. The film is not molded, as is the molten web of vacuum forming, but rather is stretched and distorted or deformed by pressure; hence, the cat-eye shape results as seen in the higher mesh counts needed for softness.

The hydro-forming film's resulting cat-eye is also the cause of the poor softness properties.

SUMMARY

In view of the foregoing, a desire developed to invent a three-dimensional micro-apertured film in the lower micro-apertured range of mesh counts from about 40 to about 75 produced by the hydroforming method that would create substantially round openings, where some would have soft petals at their apex, in order to achieve adequate fluid acquisition and improved, even superior, softness properties.

Each of the above forming methods have certain advantages in regard to the final product. The methods of the present invention provide a combination of these advantages.

An illustrative aspect of the present invention provides a method of processing a polymeric web having a substantially planar surface. The method comprises providing a forming screen configured for supporting and moving with the web in a machine direction. The forming screen has a screen wall with a plurality of elliptical screen openings formed therethrough. Each screen opening has a major axis dimension perpendicular to the machine direction and a minor axis dimension parallel to the machine direction. The method further comprises continuously depositing the web onto the forming screen so that the web is supported by the screen wall and so that the web and the forming screen wall move together in the machine direction. The web and forming screen wall are passed through a water stream having a pressure level sufficient to cause the web to be forced into the screen openings. This forms localized protrusions extending from the planar surface of the web, each protrusion having an apex, an opening at the apex, and an elliptical cross-section parallel to the planar surface of the web. The elliptical cross-section has a protrusion axis ratio. In particular embodiments, the screen opening axis ratio is selected so as to produce a desired protrusion axis ratio.

Another illustrative aspect of the invention provides a film comprising a polymeric web having first and second opposing, substantially planar web surfaces. The film further comprises a plurality of three dimensional perforations through the polymeric web. Each three dimensional perforation comprises a hollow protrusion extending from the first planar web surface. Each protrusion has an apex, an opening at the apex having a circumference defined, at least in part, by a plurality of irregularly shaped petals, and an elliptical cross-section parallel to the planar surface of the web. The elliptical cross-section has a protrusion axis ratio in a range of 0.65 to 1.35.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

FIG. 14 is a cross-sectional view of a 254 micron segment of 43.5 mesh hydro-formed three-dimensional micro-apertures of this invention which achieve desired softness being perceived by touch of having an 87 CSP mesh perception.

DETAILED DESCRIPTION

Figure 1:
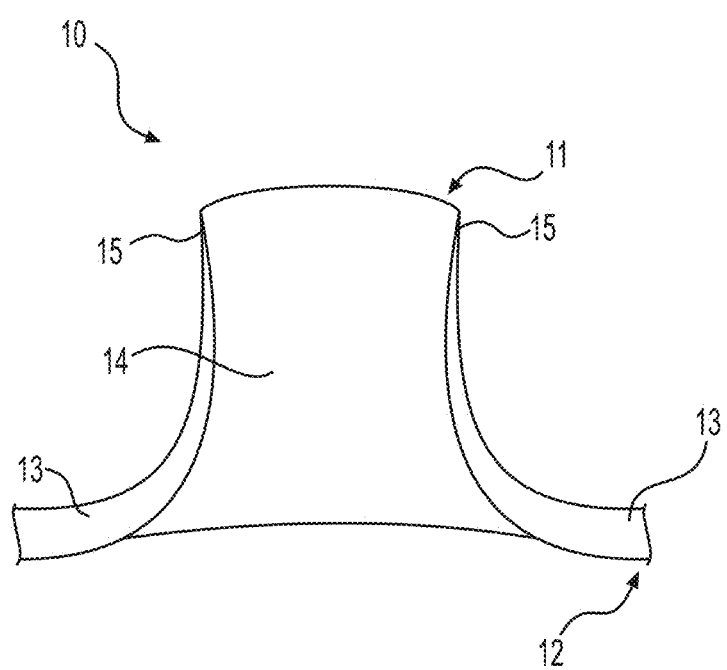
FIG. 1 is as depiction of a cross-section view of a single vacuum formed three-dimensional micro-aperture with male side up.

An "aperture" is defined as an opening in a planar web, and typically for the primary applications of this invention a web of polymeric film, such that if the web of film was black or otherwise made substantially opaque, one can see light passing through the opening. The aperture is a three-dimensional opening with a through hole beginning in the female plane of interconnected film (lands) and extending to a second plane at the apex of the openings. The collection of aperture openings in a pattern will thus have an 'open area' for the film web per square unit. A 'Per Square Inch' area unit will be utilized herein.

A "three-dimensional aperture" is defined as a protruding opening in a web. The body of the three-dimensional aperture does not entirely lie in the plane of the web as would a two-dimensional opening. The three-dimensional aperture has a base and a distal end, or apex, resulting from the three-dimensional aperture protruding in the Z direction away from the original base plane of the web and terminating at its distal end or apex in a second plane. The three-dimensional aperture at the distal end, or apex, of the protrusion will have an opening with dimensions in the X-Y directions that will be less than the dimensions of the protrusion's base opening on the original base plane of the web. Therefore, most three-dimensional apertures are at least somewhat conical or funnel-like.

To be considered 'three'-dimensional within the terms of this art, generally the distal end plane and the original base plane are spaced apart by an expansion distance, or 'loft', of at least about 40 microns. This distance is added to the original web's top-to-bottom Z direction dimension, or web thickness, due to its Z direction expansion caused by forming the protruding three-dimensional apertures.

Within the definitions applicable to this inventive art, it must be noted that three-dimensional apertures formed, for example, by hot needle penetration or other methods that might create a thickened grommet or gathered ends or flaps or hot frictional drag fragments from the web into or onto the vicinity of the aperture's perimeter, or other results of causing a thickened perimeter such that top-to-bottom Z direction may have expanded to close to 40 microns, will not be considered as belonging within the definition here-in for the term "three-dimensional aperture" since they lack the side-walls of the conical or funnel-like shape.

"Three-dimensional micro-aperture" is defined as a three-dimensional aperture of fine scale or small dimensions. Fine or small is best delimited by mesh. Three-dimensional apertures in a pattern of a mesh count of less than 30 are usually called in the art 'three-dimensional macro-apertures'; hence, three-dimensional apertures in a pattern of a mesh of greater than 30 are commonly called in the art 'three-dimensional micro-apertures'. Logically, to fit more three-dimensional apertures in an aligned length of one inch they must be smaller; hence, higher mesh requires the smaller three-dimensional micro-apertures. Logically then, mesh counts lower than 30 are used to comprise patterns of "macro-apertures". Mathematics and common sense will guide the selection of mesh combinations of formed films with both micro-apertures and macro-apertures.

"Mesh" and/or "mesh count" is a term derived from woven screens, like the ones used in Curro '518. The number of three-dimensional apertures that can be counted within one inch of distance along a line, where the three-dimensional apertures are aligned in a row, is the mesh count.

"Lands" occur between the three-dimensional apertures because the three-dimensional aperture's base opening's perimeter must be surrounded by interconnected portions of the web existing in the space between the apertures. The measurement of the space between three-dimensional apertures comprised of the material of the land defines the 'land width'. These lands between the three-dimensional apertures remain interconnected in the original plane of the web. The three-dimensional aperture's openings at their distal end, or apex, have a perimeter as well; but, there is no interconnected web in this second plane. The lands only exist in the original base plane of the web from which the apertures protrude. This is also known in the art as 'female' side. The essentially common plane of the aperture's protruding apex at the extended opening is known as the 'male' side.

If a film web comprising a pattern of three-dimensional micro-apertures is to be used as a topsheet in an absorptive device, then a pattern of macro-apertures may be introduced. In this instance, each micro-aperture has a land width around it, but the pattern of higher mesh count micro-apertures becomes the land width surrounding the lower mesh count of macro-apertures.

While micro-apertures can reduce surface wetness during use, they are not by themselves alone sufficient in opening size to move the volumes of fluids introduced to a topsheet; hence, macro-apertures may be added for that function while the micro-apertured lands primarily provide for a comfortable tactile impression.

These lands, being interconnected in the original plane of the web, serve to maintain the web's integrity and strength. Narrow land widths reduce the land area which helps to reduce residual wetness after use in an absorptive device. However, narrow land widths can cause weaker film strength, thus one skilled in the art of making three-dimensional apertured formed films will understand that a balance between performance and strength must be maintained.

Since formed films are formed on forming screens, it is also a factor in the art that the screen must have a survival integrity. This must be achieved by balancing land width area to opening area and screen thickness so the screen can have a useful and economical life in the variety of stresses applied by a variety of formed film processes. Furthermore, the various methods to fabricate screens have limitations which require the harmonizing of land width, total open area and thickness.

"Pattern" is defined as the geometric array generated by the combination of three-dimensional apertures and the lands between them. For the most useful micro-aperture patterns, the aperture shape is round and positioned in an array formed by 60 degree equilateral triangulation. The aligned apertures are aligned in the Transverse Direction (TD) and thus the equilateral triangle array cause the apertures in the Machine Direction (MD) to be staggered. A square pattern or other patterns known in the art may also be utilized. If the aperture shape is a hexagon, and the land width is held to a common width, then the positioning of hexagons in a pattern naturally results in a 60 degree equilateral triangle configuration.

In the broader scope of three-dimensional macro-aperture patterns, aperture shape geometries such as triangles, squares, pentagons, hexagons, polygons, circles, ovals, ellipses and the like can be utilized. They are placed in close proximity in an array which usually results in the narrowest possible land width. It is also desirable, whenever possible, that the land width is uniform throughout the pattern. The full extent of combinations of geometries and land width possibilities from the formed film art are too vast to itemize. Therefore, only the specifications relating to the inventive pattern will be discussed herein with the belief that one skilled in the art of making three-dimensional apertured films will not require this exhaustive teaching in order to understand the inventive departure from the prior art.

A forming "screen" apparatus within the formed film art is typically a cylinder or belt which rotates over a stationary slot. The slot area provides the zone where a pressure differential is applied to form the film into the pattern of the forming screen's apertures. Screens can be produced by a variety of methods. These methods include etching, photo-etched and laminated, electroplated, mechanically engraved or laser engraved from metal or non-metallic materials.

In most types of screens commonly utilized in formed film processes, screen apertures will be aligned in either the X direction or the Y direction of plane of the web which will be formed to replicate a percentage of the screen's three-dimensional aperture pattern. The Y direction is typically called the Machine Direction (MD) whereas the X direction is called the Transverse Direction (TD). This correlates to the absorptive device where the MD will be the front waist to back waist direction and the TD will be the left leg cuff to right leg cuff direction.

Three-dimensional apertures aligned in the MD are seldom used for topsheets in the absorptive device art, which comprises the vast majority of applications for this inventive art.

This is because the aligned three-dimensional apertures create tear initiation lines and the tearing of topsheets or other layers for absorptive devices is undesirable. Therefore, it is common in modern absorptive devices that in the MD of the pattern the three-dimensional apertures are not aligned but are staggered. In the preferred embodiment of this invention all three-dimensional apertures, both the micro-apertures and macro-apertures, are to be considered as always being aligned in the TD and staggered in the MD.

A "Compression Sensor Point" (CSP) is defined as a protrusion in web which can be detected by the sensory nerves in the skin when the skin comes into contact with web with some amount of contact pressure and shear motion. Quoting from, Ahr, U.S. Pat. No. 4,463,045, a prior art patent where protrusions on the film's surface were generated to yield a soft "cloth-like" tactile impression, "Experience has demonstrated that a more cloth-like or fiber-like tactile impression is perceived in macroscopically expanded three-dimensional plastic webs which meet the aforementioned amplitude criteria whether the surface aberrations comprise protuberances . . . . This is believed to be due to the fact that in either case the surface of the web is divided into at least two distinct planes separated from one another by a distance of at least 0.2 mils (i.e., 0.0002 inches). In the case of protuberances, it is the tops of the aberrations which contact the observer's skin . . . . Because said division is carried out in a fine microscopic pattern, it is believed that only the reduced area of contact with the uppermost surface of the web and not existence of the pattern is tactilely perceived."

Referring further to the prior art, U.S. Pat. No. 4,629,643 to Curro et al. ("Curro '643"), describes tactile function derived from micro-apertures, and this instance, those made by hydro-forming, as follows: "The present invention has further relation to such webs exhibiting a fine scale pattern of discrete surface aberrations, each of said surface aberrations having its amplitude oriented substantially perpendicular to the surface in which said surface aberration originates. A tiny aperture (micro-aperture) is provided substantially coincidental with the maximum amplitude of each surface aberration. The discontinuity created by the aperture at the peak of each of the surface aberrations substantially reduces the resistance to both compression and shear of each individual surface aberration. In addition the volcano-like edges formed at the periphery of each micro-aperture are typically in the form of thin, irregularly shaped petals which not only reduce the total contact area with the user's skin, but which are also easily deflected when relative movement with the user's skin occurs. Thus micro-apertured webs of the present invention exhibit a significantly improved tactile response. In particular, the tactile response experienced when the user's skin contacts the volcano-like edges existing at the peak of each aperture surface aberration is a much softer sensation than that experienced with similar fine scale patterns of surface aberrations which are entirely unapertured. This difference in tactile impression is most pronounced in shearing actions, i.e., when the web's contact with the skin involves lateral movement relative to the skin rather than simple compressive movement perpendicular to the skin."

Thus the term CSP, as used herein, is derived from this teaching, that the skin's sensory nerves detect the protrusion (aberration) in compression combined with a shear force when contacting the skin. A requirement, therefore, for the three-dimensional micro-apertured film of this art, and any related prior art, is that the method's mechanism to cause the expansion also causes some amount of thinning, with some portions fibrillating, around the three-dimensional aperture's distal end opening's perimeter at its apex.

Another requirement for softness is the number of CSP's that can be felt collectively. Typically hydro-formed micro-apertures of a mesh count of 75 to 140, even with a cat-eye aperture shape, are felt collectively. While the high cat-eye ratio causes the aperture to be felt as a single CSP, at CSP counts above 75 mesh they will yield a collective sensation of softness. However, at CSP counts below 75 with the cat-eye shape causing the hydro-formed micro-apertures to be felt more individually, they will yield a harsh or rougher tactile impression.

When three-dimensional micro-apertures of 40 to 75 mesh become round, however, as with the vacuum forming process, then the spacing of the diameter of the micro-aperture yields a CSP at both sides of the aperture. This creates a CSP count of about twice the mesh count where a 60 mesh pattern of round apertures, for example, actually yields a 120 mesh CSP count for soft tactile impression. A 40 mesh yields a CSP count of 80, a 43.5 mesh a CSP count of 87 and so-forth. This is why the round holes of 40 to 75 mesh from the vacuum formed films feel soft, and why the hydro-formed films of those mesh counts needed to be changed from the cat-eye shape to round in order to feel soft.

As discussed above, the formation of films having three dimensional apertures is known in the art and the primary methods of producing such films are vacuum-forming and hydro-forming processes. Both of these methods produce small surface protrusions having openings at their apexes. As described in Curro '518 and Curro '643 (the "Curro Patents"), however, hydroforming has the additional benefit that these openings exhibit petal-shaped edges, which, it is believed, enhance the apparent softness of the film. It has been found, however, that hydro-forming methods such as those described by Curro produce ovate apertures having a longer dimension in the machine direction (MD) than in the transverse direction (TD). This is unlike the vacuum forming process, which can be used to produce virtually circular holes.

The present invention provides a method that produces films with circular or near-circular three dimensional apertures while maintaining the tactile advantage of the petal-shaped edges produced by hydro-forming. This is accomplished, at least in part, through the use, in a hydroforming process, of screens having elliptical holes configured and oriented to produce apertures having a desired ratio of their MD and TD dimensions.

The paragraphs that follow describe the methods and products of the prior art.

Referring now to FIG. 1, a cross-section of a single vacuum formed film three-dimensional micro-aperture 10 formed in a generally planar web is shown. Micro-aperture 10 has a male side plane 11 and a female side plane 12. Aperture 14 is continuous from plane 12 to plane 11 forming a through-hole. The distance between male side plane 11 and female side plane 12 is the Z-direction height of the vacuum formed micro-aperture which is commonly called the "loft" of the formed film. The vacuum formed film three-dimensional aperture has lands 13 which may be interconnected to lands of adjacent vacuum formed film three-dimensional micro-apertures (not shown) which define the female plane 12. The film mass of lands 13 continues on to become the sidewall of aperture 14. Note that they continually become thinner with the thinnest portion 15 culminating at the aperture's opening at its apex on plane 11. The thinned portion 15 of the vacuum formed film three-dimensional aperture will be generally rounded and smooth. Due to the insufficient pressure differential of vacuum and the phase change from molten to solid while forming in the vacuum forming process, the thinned portion 15 does not fibrillate to form the petal-shaped edge described in the Curro Patents.

Figure 2:
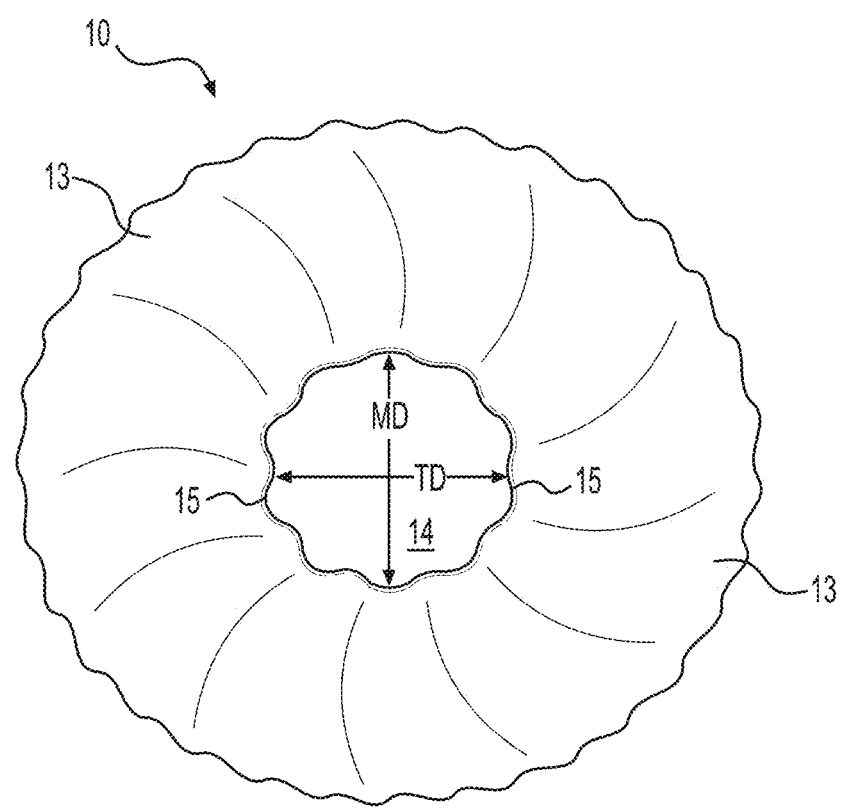
FIG. 2 is a depiction of a plan view of (looking down on) a vacuum formed three-dimensional micro-aperture with male side up.

FIG. 2 shows a plan view of the three-dimensional micro-aperture 10 looking down upon the male side plane. Aperture 14 is oriented with the MD top-to-bottom and the TD right-to-left. Lands 13 and the film mass of the lands 13 extend up to thinned tip 15 surrounding the micro-aperture's through-hole 14. Through-hole 14, when formed by the vacuum forming process, will generally have substantially equal dimensions in the MD and TD; i.e. an essentially circular shape after forming. Stresses applied by transferring the web downstream in the Machine Direction may act to stretch and elongate the through-hole micro-aperture a bit; but, as formed, it is virtually circular.

Figure 3:
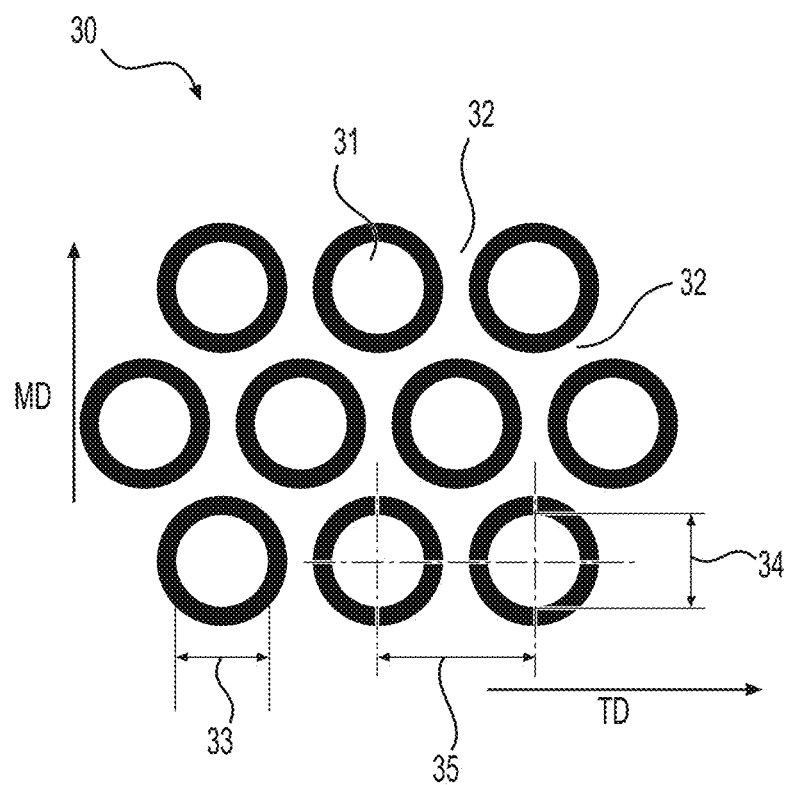
FIG. 3 is a schematic view of a segment of a prior art forming screen with a pattern of round micro-apertures.

FIG. 3 shows a schematic of a section 30 of a typical forming screen pattern designed to make micro-apertures. For the example used for describing this invention, this screen is a 60 mesh screen. Screen section 30 has a 60 degree equilateral triangulated pattern of micro-apertures 31 with the aligned micro-apertures aligned in the TD and the MD micro-apertures being staggered. Micro-apertures 31 are surrounded by lands 32. The land width is substantially equal on all side. For this example land width is 152 microns. TD aperture diameter 33 is about 250 microns and MD aperture diameter 34 is equal at about 250 microns. The center-to-center spacing 35 of micro-apertures aligned in the TD is 424 microns.

The center-to-center spacing 35 value can be used to determine 'mesh'. Converting 424 microns to inches yields 0.0167 inches. Dividing 1.0 inch of aligned aperture distance divided by 0.0167 inches of center-to-center spacing yields the 60 mesh count. The 60 mesh screen of FIG. 3 having the micro-apertures in a 60 degree equilateral triangle array yields about 4,140 apertures per square inch of forming screen and will yield about the same value of micro-apertures per square inch for the films that are formed on this forming screen. The screen open area is about 31%.

Figure 4:
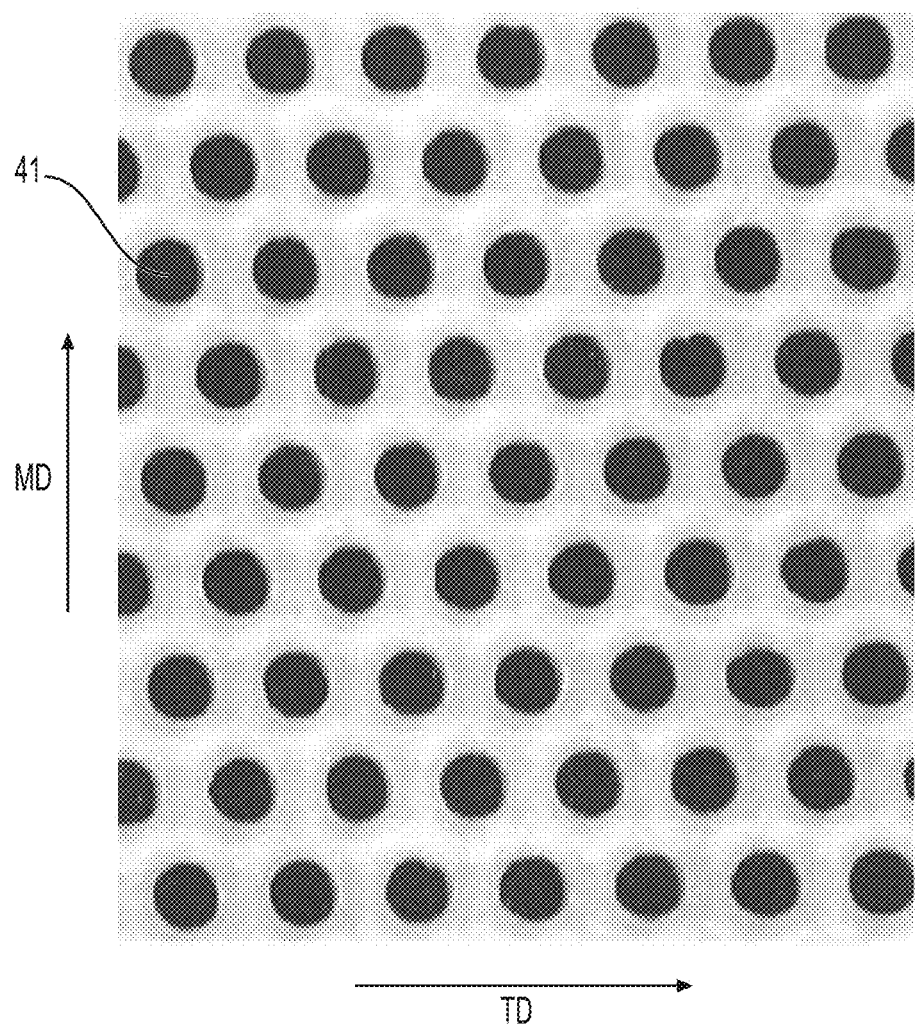
FIG. 4 is a micro-scope photograph of three-dimensional micro-apertures formed on the screen of FIG. 3 by the vacuum forming process.

FIG. 4 shows a micro-scope photograph of a plan view of a 60 mesh vacuum formed three-dimensional micro-apertured film made from the screen of FIG. 3. Note the round aperture shapes 41 of the vacuum formed film. The film open area for this vacuum formed micro-apertured film is about 24.5%.

Figure 5:
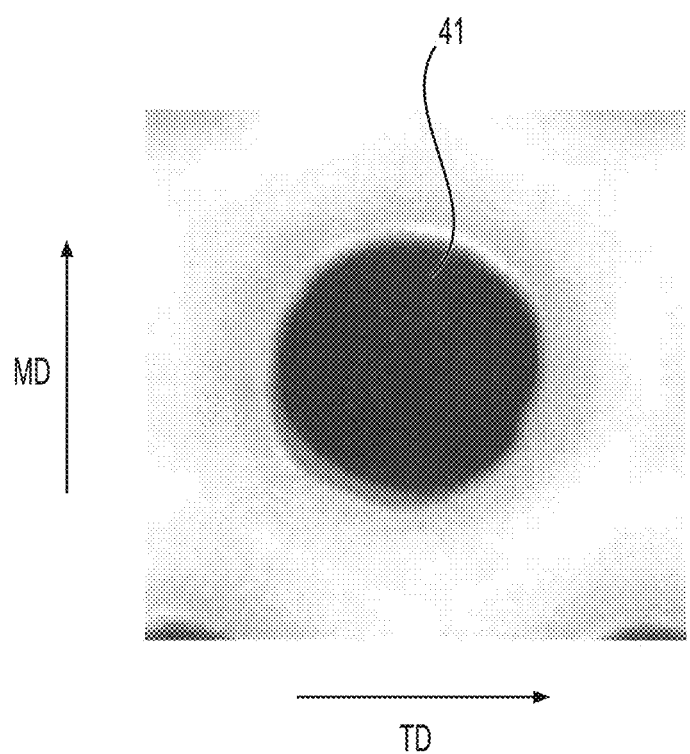
FIG. 5 is an enlarged micro-scope photograph of a single vacuum formed three-dimensional micro-aperture formed on the screen of FIG. 3 by the vacuum forming process.

FIG. 5 shows an expanded micro-scope photograph of a single vacuum formed film three-dimensional micro-aperture 41 of the vacuum formed film of FIG. 4. It has a diameter of about 202 microns in both the MD and TD. The vacuum forming process generally achieves a film aperture diameter that is from about 60% to 85% of the screen's aperture diameter. In this example, the film's micro-aperture diameter is about 80% of the screen's aperture diameter. Since the round aperture diameter has virtually equivalent radii in both the MD and TD, that radius corresponds to area $(\pi R^2)$; hence, it can also be said that the film's aperture area is also about 80% of the screen's aperture area.

Figure 6:
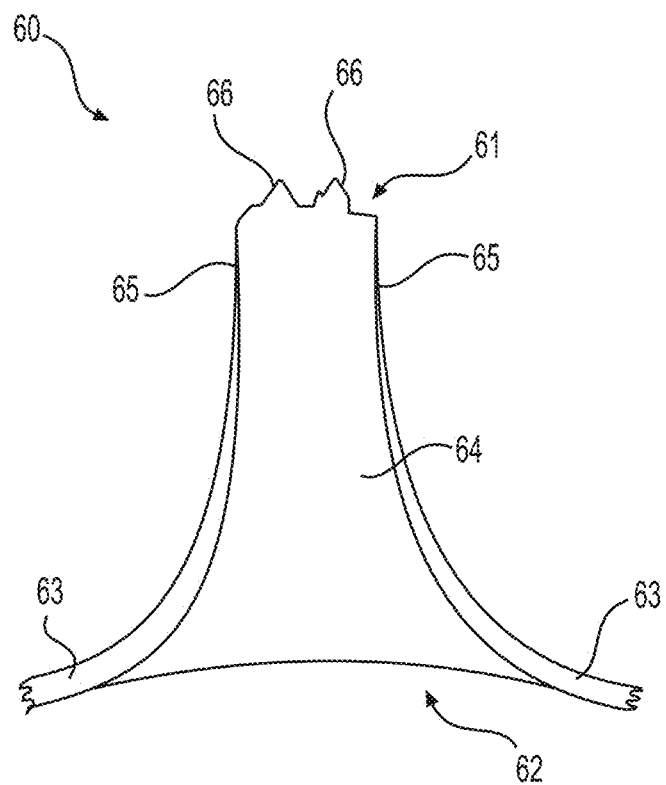
FIG. 6 is a depiction of a cross-section view of a single prior art hydro-formed three-dimensional micro-aperture with male side up.
Figure 7:
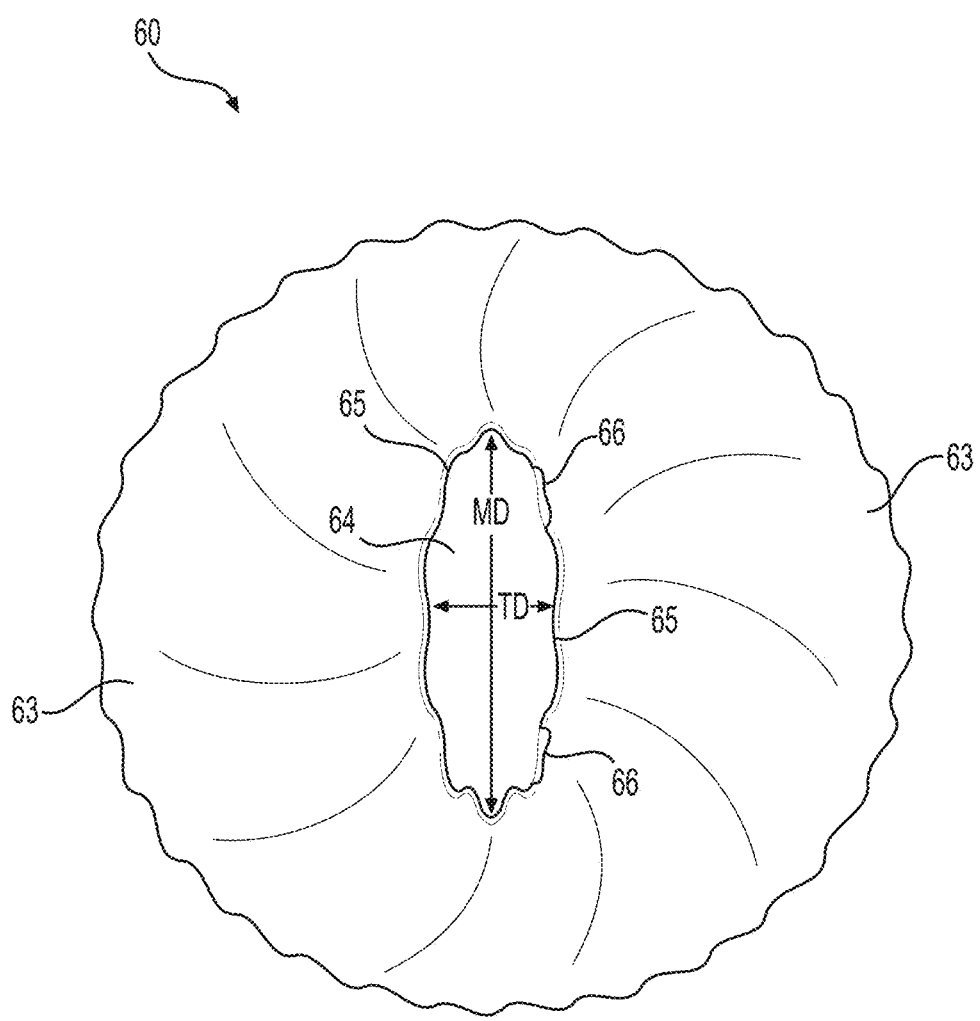
FIG. 7 is a depiction of a plan view of a prior art hydro-formed three-dimensional micro-aperture with male side up.

FIGS. 6 and 7 illustrate cross-sectional and plan views of a single three-dimensional micro-aperture 60 formed using a hydro-forming method such as that described in the Curro Patents. Micro-aperture 60 has a male side plane 61 and a female side plane 62. Micro-aperture 64 is continuous from plane 62 to plane 61 forming a through-hole. The distance between male side plane 61 and female side plane 62 is the Z-direction height of the hydro-formed micro-aperture is commonly called the "loft" of the formed film. The hydro-formed film three-dimensional micro-aperture has lands 63 which are interconnected to lands of adjacent hydroformed film three-dimensional micro-apertures (not shown) which form the female plane 62. The film mass of lands 63 continues on to become the sidewalls of aperture 64. Note that they continually become thinner with the thinnest tips 65 culminating at the aperture's opening apex on plane 61.

These thinned tips of the hydro-formed film three-dimensional micro-apertures will often form fibrillations 66 called 'petals' in the prior art as shown by the Curro Patents.

The plan view of FIG. 7 shows the three-dimensional micro-aperture 40 looking down upon the male side plane 61. Micro-aperture 64 is oriented with the Machine Direction (MD) top-to-bottom and the Transverse Direction (TD) right-to-left. Lands 63 and the film mass of the lands 63 extends up to thinned tip 65 surrounding the micro-aperture's through-hole 64. As will be demonstrated hereafter, the through-hole 64, when formed by the prior art hydroforming process, will have substantially unequal dimensions in the MD and TD; i.e., an ovate or "cat-eye" shape.

Figure 8:
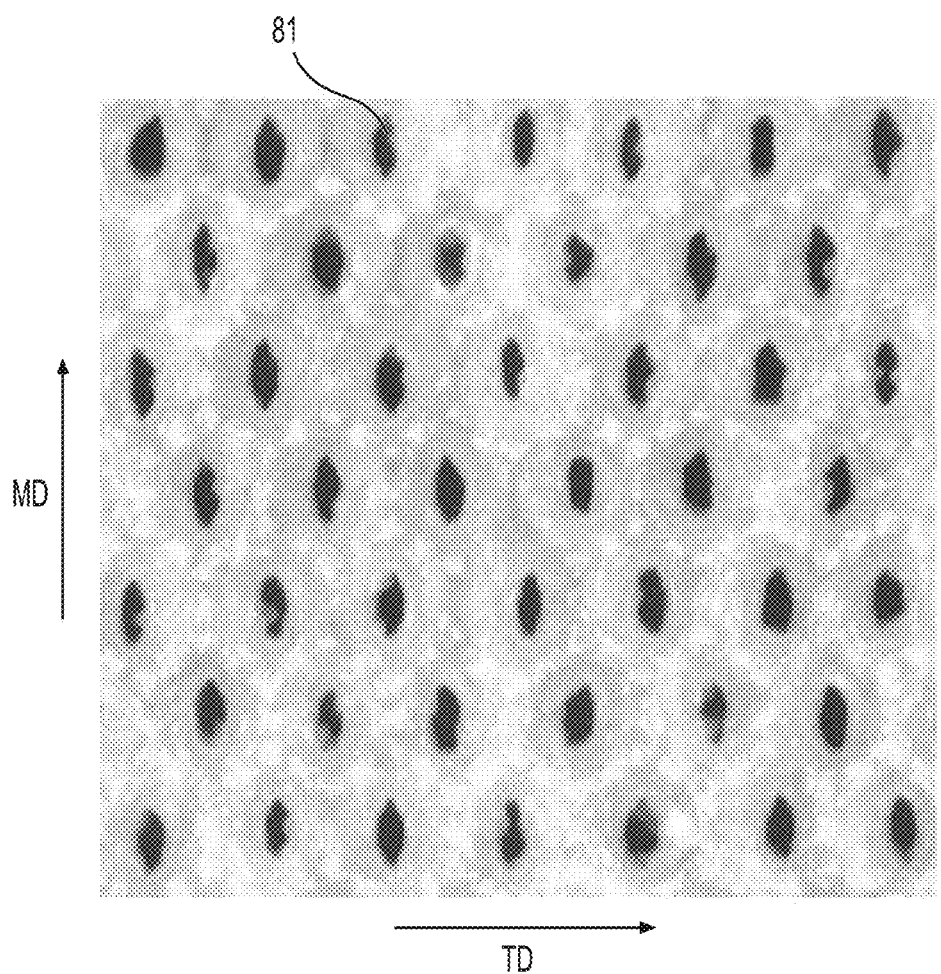
FIG. 8 is a micro-scope photograph of prior art hydro-formed micro-apertures formed on the screen of FIG. 3 by the hydro-forming process.

FIG. 8 shows a micro-scope photograph of a segment of a prior art 60 mesh hydro-formed three-dimensional micro-apertured film made using the screen of FIG. 3. Note that the film apertures 81 are much smaller and have a greater MD axis than the TD axis. This is the cat-eye shape. The cat-eye shape yields an "axis ratio" whereupon the smaller axis is divided into the larger axis. The illustrated hydro-formed film has an open area of about 9% and a range of axis ratios from about 1.85 to 2.12, even though it was made on the same screen as was the vacuum-formed film shown in FIG. 4.

Cat-eye aperture opening area corresponds to its radii, as well ($\pi[Ra \times Rb]$). It is known in the art of production of formed films that hydro-forming will only produce a film aperture area with about 25% to 45% of the forming screen's aperture area; hence, the hydro-formed apertures are significantly smaller than corresponding apertures of a vacuum-formed film produced on the same screen. The reduction in area is partly due to cat-eye shape of the loss of the TD radius dimension, but also because the aperture is generally smaller overall.

This narrowing effect of the cat-eye micro-aperture shape is the primary cause for the loss of the desired softness factor for mesh counts from about 40 to 75 mesh. This will be discussed in greater detail hereafter, using FIGS. 13 and 14.

It will be understood that the axis ratio of the three dimensional aperture tends to be constant for cross-sections through the protrusion parallel to the planar surface of the web. This is particularly true of the upper portion of the volcano-shaped protrusion up to and including the actual perforation at the apex of the protrusion, which is the area that affects tactile impression when in contact with skin.

Figure 9:
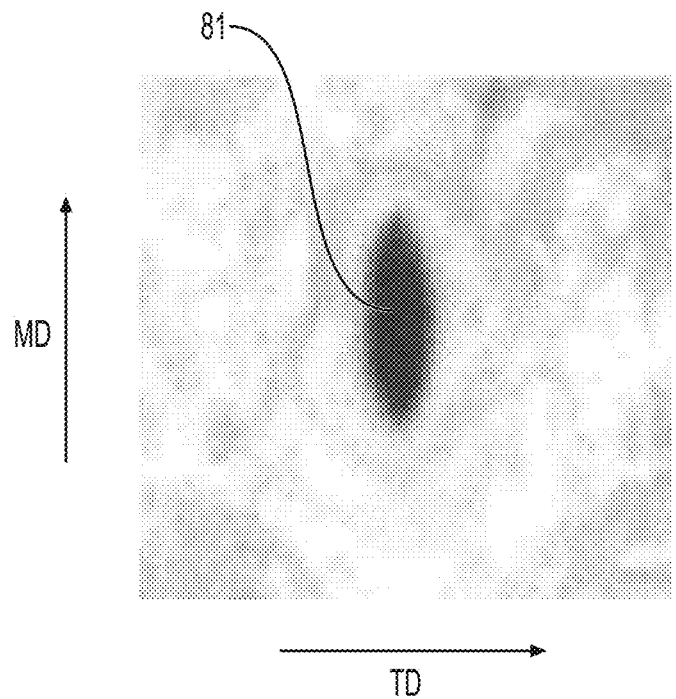
FIG. 9 is an enlarged micro-scope photograph of a prior art single hydro-formed three-dimensional micro-aperture formed on the screen of FIG. 3 by the hydro-forming process.

FIG. 9 shows an enlarged micro-scope photograph of a single prior art micro-aperture 81 from FIG. 8 made by the hydro-forming process on the screen of FIG. 3. It has an MD axis dimension of about 195 microns with a TD axis dimension of about 95 microns. This yields an axis ratio of about 2.05. The axis ratio of hydro-formed three-dimensional micro-apertures of the prior art will vary depending on a diversity of screen patterns and run conditions.

It is known by those of ordinary skill in the art of hydro-forming that larger micro-apertures of lower mesh count values will have a lower axis ratio due to having more space in the forming screen aperture in which to form the film aperture. Stating generalizations derived from data with some distribution, a 40 mesh axis ratio of the prior art process of hydro-forming micro-apertures may be as low as about 1.45 and a 140 mesh axis ratio can be as high as 2.35.

Additionally, many other variables of the hydro-forming process conditions such as water pressure, water temperature, the rate of screen rotation, the polymer blend being utilized, and the like will create variation; but, none of these condition manipulations have been found to successfully eliminate the cat-eye shape and its resulting axis ratio.

Therefore, the full axis ratio range for prior art hydro-formed three-dimensional micro-apertures of 40 mesh to 140 mesh is about 1.45 to generally about 2.35. In order to achieve the similarly round apertures of vacuum forming and to gain the advantages of added softness from petals derived from the hydro-forming process, an inventive step was required to virtually eliminate the cat-eye shape of hydro-formed micro-apertures.

The present invention provides a novel variation in the hydroforming process. In this variation, the openings in the screen used to form the three dimensional apertures are specifically tailored to counter the cat-eye problem of previous methods.

As in typical hydroforming processes, the methods of the invention provide for continuous disposition of the film on a moving, perforated forming screen. Forming screens are typically a rotatable hollow cylinder or a belt that is configured so that the perforated wall of the screen passes over a stationary slot (or slots). After deposition on the screen, the film is passed beneath a series of aligned high pressure water nozzles, the pressure to which is supplied by a high pressure water pump system. The nozzles are designed to deliver a somewhat flat spray pattern and spaced so the edge of the spray pattern of each nozzle slightly overlaps with the edge of the adjacent nozzle so no gaps in applied pressure exist down the length of the system.

The high pressure water stream causes the film to be pressed into and through the openings in the screen, so that they adopt, to some extent, the three dimensional shape of the perforation. As this occurs, the film is stretched so that it is thinned and eventually ruptures to form a perforation at the apex of the deformation. The film is then removed from the screen with the protrusions remaining intact. The film can then be further processed (e.g., through the addition of further micro or macro-perforations) or rolled for storage or transport.

As discussed above, previously used hydroforming methods of this type produced elongated cat-eye shaped apertures in the web, the major axis of these apertures being aligned with the direction of motion of the film web and the forming screen. The elongate shape is thought to result from the use of regularized (typically circular) screen openings.

The present method differs from previous hydroforming methods in that the configuration of the screen perforations are adapted to the characteristics of the process and the film material so as to reduce or eliminate the elongation effect. In general, this involves making the screen openings elliptical (or similar ovate shape) with their minor axes aligned in the machine direction and their major axes aligned in the transverse direction. The exact ratio of the major to minor axis is a function of the material, speed of the manufacturing line, water pressure and temperature, etc.

The water temperature is typically elevated to 180° F. to soften, but not melt, the film; but temperatures within the range of 120-200° F. can also be functional. The water nozzles are placed about 4-5 inches away from the rotating screen cylinder, but distances of 2-10 inches may also be applied. The film web caliper can range from 12-70 microns in thickness with common gauges ranging from 22-24 microns. The web can be comprised of a variety of olefin polymers in monolayer or coextruded multiple layers.

The methods of the invention can be used with films formed from any suitable polymer. Particularly suitable polymers include, but are not limited to, polyethylene, low density and ultra-low density polyethylene, polypropylene, linear low and medium density polyethylene, metallocenes, block copolymers, vinyl acetate copolymers, and various elastomers. These can be used either blended into monolayer films or extruded independently or formed in coextruded films having two layers to five layers or more as one skilled in the art of film extrusion may design to meet a variety of film attribute requirements.

Figure 10:
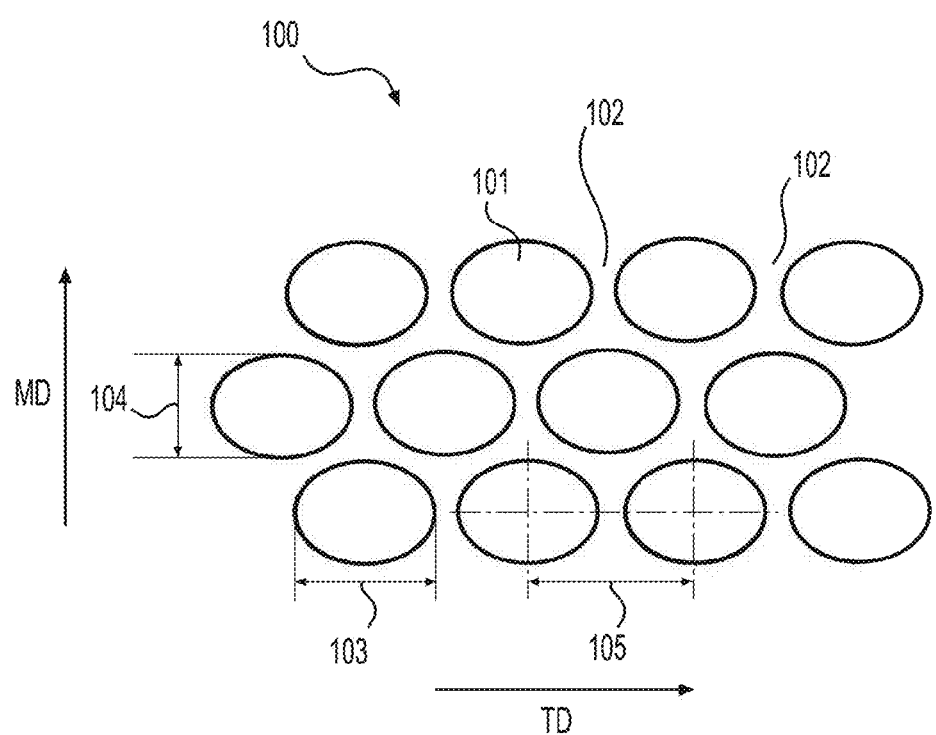
FIG. 10 is a schematic of an example hole of a forming screen with micro-apertures in the shape of this invention.

Referring now to FIG. 10, a portion of an exemplary forming screen 100 for use in the methods of the invention is shown. The exemplary screen 100 is a 43.5 mesh screen. The apertures 101 of screen 100 have a major axis 103 greater than the minor axis 104 by a factor (i.e., the axis ratio) of about 1.35. Screen 100 has apertures 101 surrounded by lands 102. The land width is preferably equal on all side. For this example land width is 102 microns. TD aperture diameter 103 is about 483 microns and MD aperture 104 is about 345 microns. The center-to-center spacing 105 of apertures aligned in the TD is 585 microns.

While the axis ratio of the illustrated example is 1.35, it will be understood by those of ordinary skill in the art that screens with axis ratios from about 1.15 to 2.50 can be utilized.

These variations may be necessary for various mesh counts, pattern arrays, or polymer blends for mono-layer films and/or coextruded films. Coextruded films can utilize from 2 to 5 layers effectively, whereupon the features of each layer are designed for specific functions in either hydro-forming aperture formation or end use requirements or both.

The center-to-center spacing 105 can be used to determine 'mesh'. Converting 585 microns to inches yields 0.023 inches. 1.0 inch of aligned aperture distance divided by 0.023 inches of center-to-center spacing yields about a 43.5 mesh count. The 43.5 mesh screen of FIG. 10 has the apertures aligned in the TD and in a staggered array in the MD. With the uniform land width this yields about 2,414 apertures per square inch of forming screen. Whereupon the screen has 43.5 apertures per inch in the TD and about 55.5 apertures in the MD, then 43.5×55.5=2,414 apertures per square inch. The screen open area is around 50%. When hydro-formed micro-apertured film is produced on forming screen 100 of FIG. 10, it will yield about the same value of apertures per square inch, depending on machine direction draws which may distort the film packing the apertures a bit closer in the TD.

To create this inventive screen of a preferred embodiment with a high open area of about 50% and a relatively high count of apertures per square inch while also having narrow land widths of 102 microns, forming screen 100 of FIG. 10 was made by the photo-etch and laminate method as taught by U.S. Pat. No. 5,562,932 to Rieker, incorporated herein by reference, with exception that the laminated layers are stacked vertically versus at an offset angle. Another preferred technique for making a forming screen as required for this invention is the method disclosed by U.S. Pat. No. 8,460,778 to Thomas et al., incorporated herein by reference, of laser engraving thermoset materials like rubber. A finish of a nickel plated coating over the rubber screen enhances the strength and thermal properties of these rubber laser engraved screens. Laser engraving a metal screen may also be plausible, as are any of the screen making methods if properly manipulated.

Figure 11:
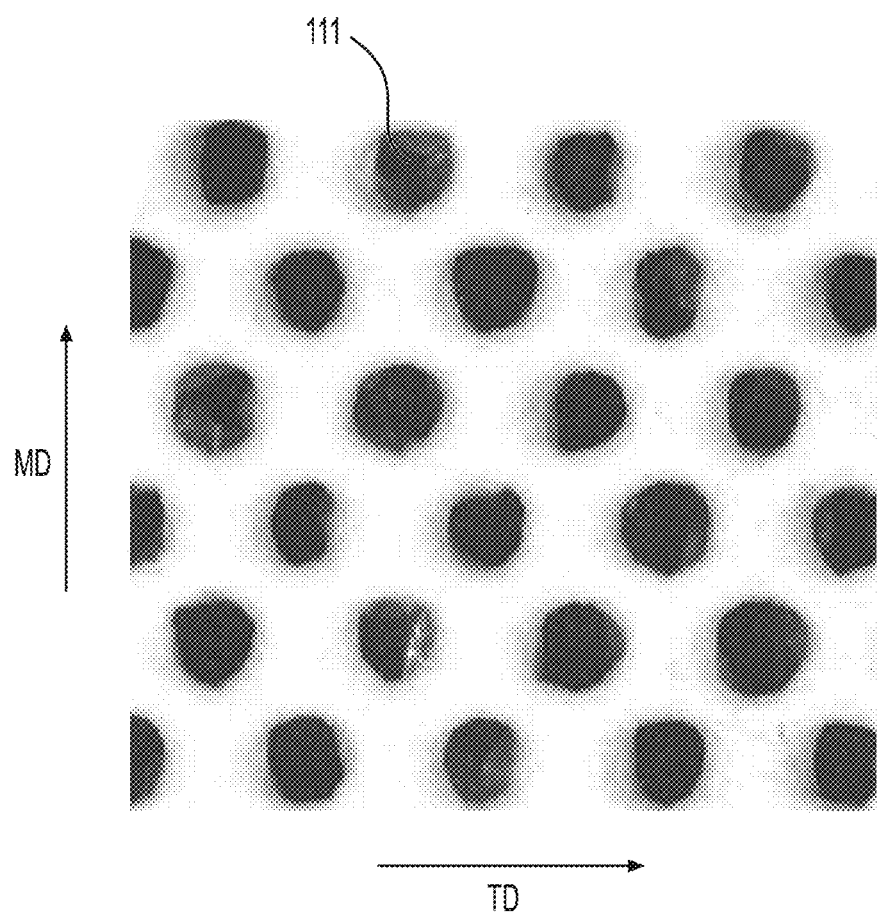
FIG. 11 is a micro-scope photograph of hydro-formed micro-apertures of this invention formed on the screen of FIG. 10 by the hydro-forming process.

FIG. 11 shows a portion of the 43.5 mesh hydro-formed film of three-dimensional micro-apertures 111 made by the hydro-forming process on the inventive screen of FIG. 10. Note that the apertures are virtually round. The open area of this inventive hydro-formed three-dimensional micro-apertured film is about 25%; hence, the hydro-forming process has created apertures 111 of about 50% of the size and open area of the forming screen apertures; and exceptionally, they have no discernable cat-eye shape but rather appear to be virtually round with essentially equivalent MD and TD axes.

Figure 12:
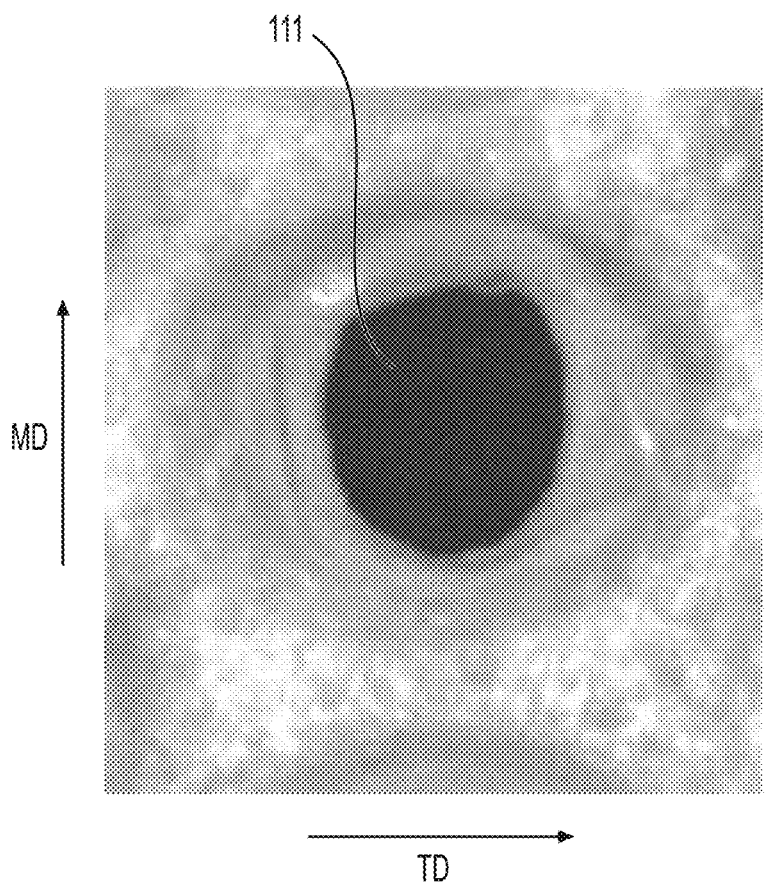
FIG. 12 is an enlarged micro-scope photograph of a single hydro-formed three-dimensional micro-aperture of this invention formed on the screen of FIG. 10 by the hydro-forming process.

FIG. 12 is an expanded micro-scope photograph of a single micro-aperture 111 from FIG. 11. The aperture 111 has an MD axis of about 292 microns and a TD axis of about the same measure of 292 microns. That yields a round hole with an axis ratio of 1.00. A few of the apertures shown in FIG. 11 have an MD axis of about 292 microns with a TD axis of about 255 microns yielding a significantly reduced, virtually round, axis ratio of about 1.15. Although measurements were taken from a much larger number of apertures than is shown in FIG. 11, no measurement made by this method has given a micro-aperture axis ratio greater than 1.35.

As mentioned earlier for the prior art of vacuum forming, which forms essentially round apertures, vacuum formed three-dimensional micro-apertures can achieve a significant degree of softness in mesh counts from about 40 to 75, but lack 'superior' softness because they lack the feature of fibrillated petals.

Figure 13:
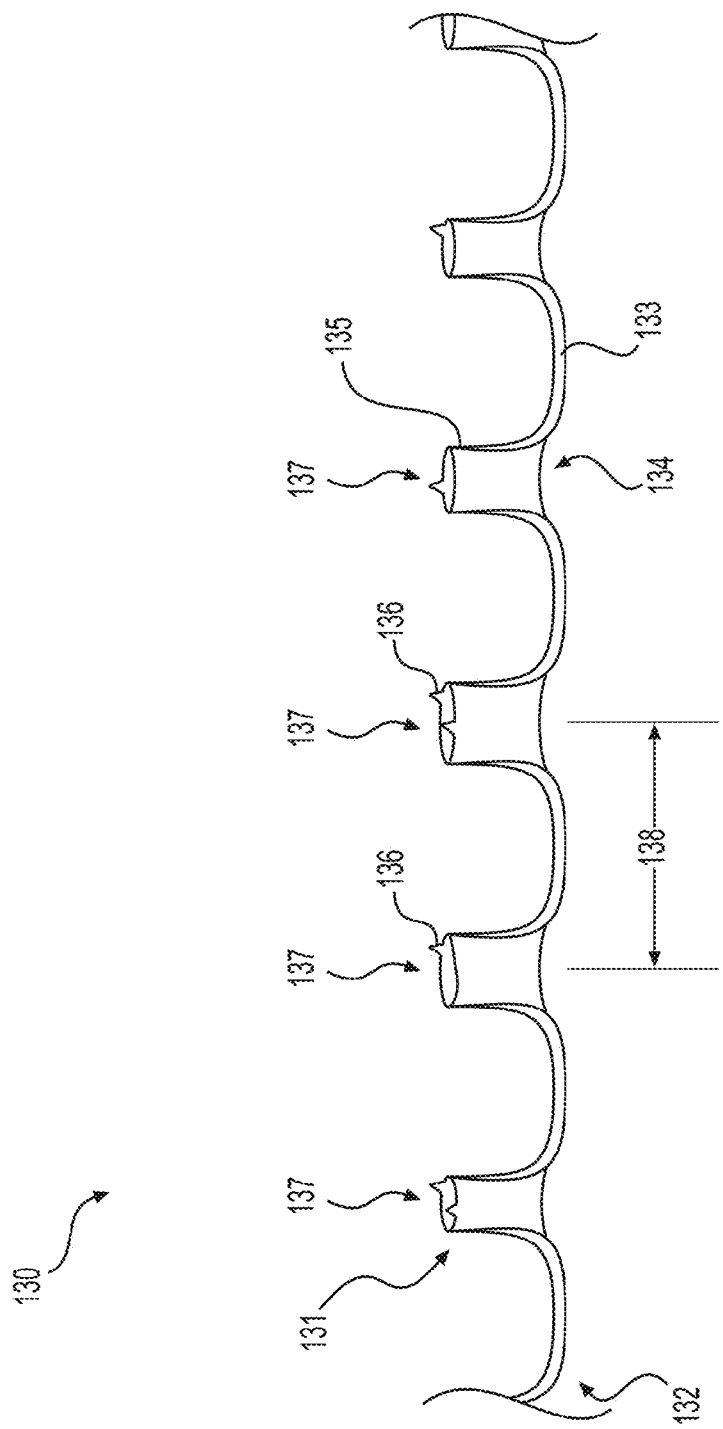
FIG. 13 is a cross-sectional view of a 254 micron segment of 60 mesh hydro-formed three-dimensional micro-apertures of prior art which lack the desired softness being perceived by touch of having only a 60 CSP mesh perception.

It was shown in the prior art that a 60 mesh films of vacuum formed three-dimensional micro-apertures are successfully marketed today as being soft and that hydro-formed three-dimensional micro-apertured films of the prior art of 100 mesh have had market success for softness. However, a 60 mesh variety of hydro-formed micro apertured film, for example, lacks the needed softness. FIG. 13 will be utilized for an explanation of that observation and FIG. 14 will show why creating a hydro-formed three-dimensional micro-aperture with a round shape, versus the cat-eye shape, is an inventive step which makes the hydro-formed micro-apertured film feel soft.

Referring now to FIG. 13 we see a cross-section of a segment of prior art hydro-formed three-dimensional micro-apertured film 130. The segment 130 is about 254 microns in length and comes from a 60 mesh pattern screen. Segment 130 has a male side plane 131 and a female side plane 132. Micro-apertures 134 are continuous from plane 132 to plane 131 forming through-holes. The distance between male side plane 131 and female side plane 132 is the Z-direction height of the hydro-formed apertures which is commonly called the "loft" of the formed film. The hydro-formed film three-dimensional micro-aperture has lands 133 which are interconnected to the lands of the adjacent hydro-formed film three-dimensional micro-apertures which form the female plane 132. The film mass of lands 133 continues on to become the sidewalls of aperture 134. Note that they continually become thinner with the thinnest tips 135 culminating at the aperture's opening apex on plane 131. These hydro-formed film three-dimensional micro-apertures have a cat-eye shape and the narrow axis width of aperture 134 shown in FIG. 13 is in the TD axis width, left to right in FIG. 13. The major axis in the MD is pointing away from the viewer of FIG. 13. Being hydro-formed some micro-apertures may have petals 136, but their softness effect is nullified by other overwhelming factors.

As defined above, a protrusion that yields sensory recognition by the skin's nerves is a "Compression Sensor Point" (CSP). It has been shown in several prior art teachings (some noted above) that the CSP's resulting from micro-apertures should be closely packed because if the CSP's are too far apart they are sensed individually and the sensation moves toward being harsh or rough. To best detect the sensation of softness the skin must detect a collective effect of protrusion tips that can compress and bend during a skin contact moment. The thinned openings at their apex, and an occasional petal, serve to provide the compression and bending mechanisms of a CSP that best provide for the sensation of softness provided they are within the range of CSP counts that yield softness. The soft CSP count where softness first occurs is generally believed to be about 80.

The primary factor to note in FIG. 13 is that since the apertures have a significant cat-eye shape with a high axis ratio, being narrow versus spread out, they become "individual" CSPs 137. With a center-to-center spacing 138 of 424 microns, these CSPs 137 are spaced apart at a CSP count of 60 mesh such that the skin can feel them as a single CSP unit versus as a collective of multiple units; and, as shown in the prior art, since the CSP count is below 80, this sensation robs the softness tactile impression, and rather, is moving toward a harsh or a rough sensation.

When the vacuum forming process produces round three-dimensional micro-apertures in the same 60 mesh count, the CSP becomes the side-wall on either side of the aperture due to the widening of the distance between the sidewalls. Thusly, a 60 mesh vacuum formed three-dimensional micro-apertured film will produce CSPs at about a about 120 mesh and it therefore feels soft, like the 100 mesh hydro-formed feels soft, as both CSP counts are above the minimum count of about 80 for softness.

Referring now to FIG. 14 segment 140 of the inventive hydro-formed three-dimensional micro-apertured film is shown. This segment 140 length is also about 254 microns. Film segment 140 has a male side plane 141 and a female side plane 142. Micro-apertures 144 are continuous from plane 142 to plane 141 forming a through-hole. The distance between male side plane 141 and female side plane 142 is the Z-direction height of the hydro-formed micro-apertures which is commonly called the "loft" of the formed film. The hydro-formed film three-dimensional micro-apertures have lands 143 that are interconnected to lands of adjacent hydro-formed film three-dimensional micro-apertures which form the female plane 142. The film mass of lands 143 continues on to become the sidewalls of aperture 144. Note that they continually become thinner with the thinnest tips 145 culminating at the aperture's opening apex on plane 141. Some thinned tips 145 have petals 146.

Micro-apertures 144 have a TD aligned center-to-spacing 148 of about 585 microns yielding a mesh count of around 43.5 mesh. Micro-apertures 144 have a MD and TD diameter of about 292 microns; and, since the CSPs 147 are in this case the thinned side-wall of micro-aperture 144, the CSP spacing, both across the aperture opening 149 and between apertures 149', is about 292 microns, which is much closer together. At 43.5 mesh the CSP 147 count of this inventive film is about 87 which is above the minimum value of 80 for softness. With the addition of the hydro-formed petals 146 greater softness may be achieved. Additionally micro-apertured films of greater than 15% open area will provide for the adequate removal of residual fluids after use. Therefore, the preferred embodiment of this inventive film depicted in FIGS. 11 and 14, having 25% open area, should provide for sufficient dryness if utilized as a topsheet.

This invention therefore provides a hydro-formed three-dimensional micro-apertured film soft enough, with enough open area to enhance removal of residual fluids to be useful as, but not limited to, a topsheet in absorptive devices such as feminine napkins, panty liners, baby diapers, adult diapers, incontinence inserts, bandages and the like, particularly when a pattern of macro-apertures are added to it.

It will be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its preferred embodiment, it is to be understood that this disclosure is only illustrative and exemplary of the present invention and is made merely for the purposes of providing a full and enabling disclosure of the invention. Many modifications to the embodiments described above can be made without departing from the spirit and scope of the invention. Accordingly, the foregoing disclosure is not intended to be construed or to limit the present invention or otherwise to exclude any other such embodiments, adaptations, variations, modifications and equivalent arrangements.

What is claimed is:

1. A film comprising:
   a polymeric web having first and second opposing, substantially planar web surfaces; and
   a plurality of three dimensional perforations through the polymeric web, each three dimensional perforation comprising a hollow protrusion extending from the first planar web surface, each protrusion having an apex, an opening at the apex having a circumference defined, at least in part, by a plurality of irregularly shaped petals, and an elliptical cross-section parallel to the planar surface of the web, the elliptical cross-section having a protrusion axis ratio in a range of 0.65 to 1.35,
   wherein the plurality of three dimensional perforations were formed using a hydroforming process, and
   wherein the localized protrusions are formed in the web in a two-dimensional pattern having a mesh count in a range of about 40 to about 75.

2. The film according to claim 1, wherein the protrusion axis ratio range is about 0.9 to 1.1.

3. The film according to claim 2, wherein the protrusion axis ratio is about 1.0.

4. The film according to claim 1, wherein the film has a compression sensor point of at least about 80.

5. A film according to claim 1, wherein the two-dimensional pattern is configured so that the localized protrusions are aligned in the traverse direction and staggered in the machine direction.

6. A method of forming a film, comprising a polymeric web having first and second opposing, substantially planar web surfaces, the method comprising:
   providing a forming screen configured for supporting and moving with the web in a machine direction, the forming screen having a screen wall with a plurality of elliptical screen openings formed therethrough, each screen opening having a major axis dimension perpendicular to the machine direction and a minor axis dimension parallel to the machine direction;
   continuously depositing the web onto the forming screen so that the web is supported by the screen wall and so that the web and the forming screen wall move together in the machine direction; and
   passing the web and forming screen wall through a water stream having a pressure level sufficient to cause the web to be forced into the screen openings, thereby hydroforming localized protrusions extending from the first planar surface of the web, each protrusion having an apex, an opening at the apex having a circumference, defined at least in part, by irregularly shaped petals, and an elliptical cross-section parallel to the planar surface of the web, the elliptical cross-section having a protrusion axis ratio in a range of 0.65 to 1.35, wherein the localized protrusions are formed in the web in a two-dimensional pattern having a maximum mesh count in a range of about 40 to about 75.

7. The method according to claim 6, wherein the protrusion axis ratio range is about 0.9 to 1.1.

8. The method according to claim 7, wherein the protrusion axis ratio is about 1.0.

9. The method according to claim 6, wherein the screen opening axis ratio is in a range of about 1.15 to about 2.50.

10. The method according to claim 6, wherein the step of providing further comprises selecting a screen opening axis ratio so as to produce the protrusion axis ratio as desired.

11. The method according to claim 6, wherein the film has a compression sensor point of at least about 80.

12. The method according to claim 6, wherein the two-dimensional pattern is configured so that the localized protrusions are aligned in the traverse direction and staggered in the machine direction.

* * * * *